(12) United States Patent
Joshi et al.

(10) Patent No.: US 8,699,660 B2
(45) Date of Patent: Apr. 15, 2014

(54) LIQUID COOLED THERMAL CONTROL SYSTEM FOR AN IMAGING DETECTOR

(75) Inventors: Ashutosh Joshi, Waukesha, WI (US); Joseph James Lacey, Waukesha, WI (US); Medy Satria, Bangalore Kanataka (IN)

(73) Assignee: General Electric Company, Schenectady, NY (US)

( * ) Notice: Subject to any disclaimer, the term of this patent is extended or adjusted under 35 U.S.C. 154(b) by 43 days.

(21) Appl. No.: 13/454,134

(22) Filed: Apr. 24, 2012

(65) Prior Publication Data

US 2013/0279648 A1    Oct. 24, 2013

(51) Int. Cl.
*A61B 6/00* (2006.01)
(52) U.S. Cl.
USPC ............................................ 378/19; 378/117
(58) Field of Classification Search
USPC .............. 378/19, 91, 114–117, 207
See application file for complete search history.

(56) References Cited

U.S. PATENT DOCUMENTS

| 5,276,630 | A * | 1/1994 | Baldwin et al. ............... 700/276 |
| 6,359,346 | B1 | 3/2002 | Kumar |
| 6,741,919 | B1 | 5/2004 | Schuster et al. |
| 7,236,562 | B2 | 6/2007 | Joshi et al. |
| 7,449,696 | B2 | 11/2008 | Joshi et al. |
| 2008/0069296 | A1 | 3/2008 | Joshi et al. |

* cited by examiner

*Primary Examiner* — Jurie Yun
(74) *Attorney, Agent, or Firm* — The Small Patent Law Group; Dean D. Small

(57) ABSTRACT

A liquid cooled thermal control system for a computed tomography (CT) detector includes a plurality of temperature sensors and a control mode selector module coupled to the plurality of temperature sensors. The control mode selector module is programmed to receive an input from the plurality of temperature sensors, identify the inputs as either valid inputs or invalid inputs, and determine an operational mode of the liquid cooled thermal control system based on the identified inputs. A CT imaging system and a method of operating a cooling system are also described.

26 Claims, 9 Drawing Sheets

| (A) 256 | (B) 254 | (C) 252 | | | | | |
|---|---|---|---|---|---|---|---|
| Heater Out | HEX Out | HEX In | Baseline | Reconfig A | Reconfig B | Protection | Mode |
| 1 | 1 | 1 |  |  |  | 1 | 4 |
| 1 | 1 | 0 |  |  | 1 |  | 3 |
| 1 | 0 | 1 |  | 1 |  |  | 2 |
| 1 | 0 | 0 |  | 1 |  |  | 2 |
| 0 | 1 | 1 | 1 |  |  |  | 1 |
| 0 | 1 | 0 | 1 |  |  |  | 1 |
| 0 | 0 | 1 | 1 |  |  |  | 1 |
| 0 | 0 | 0 | 1 |  |  |  | 1 |

0=sensor good; 1=sensor fail

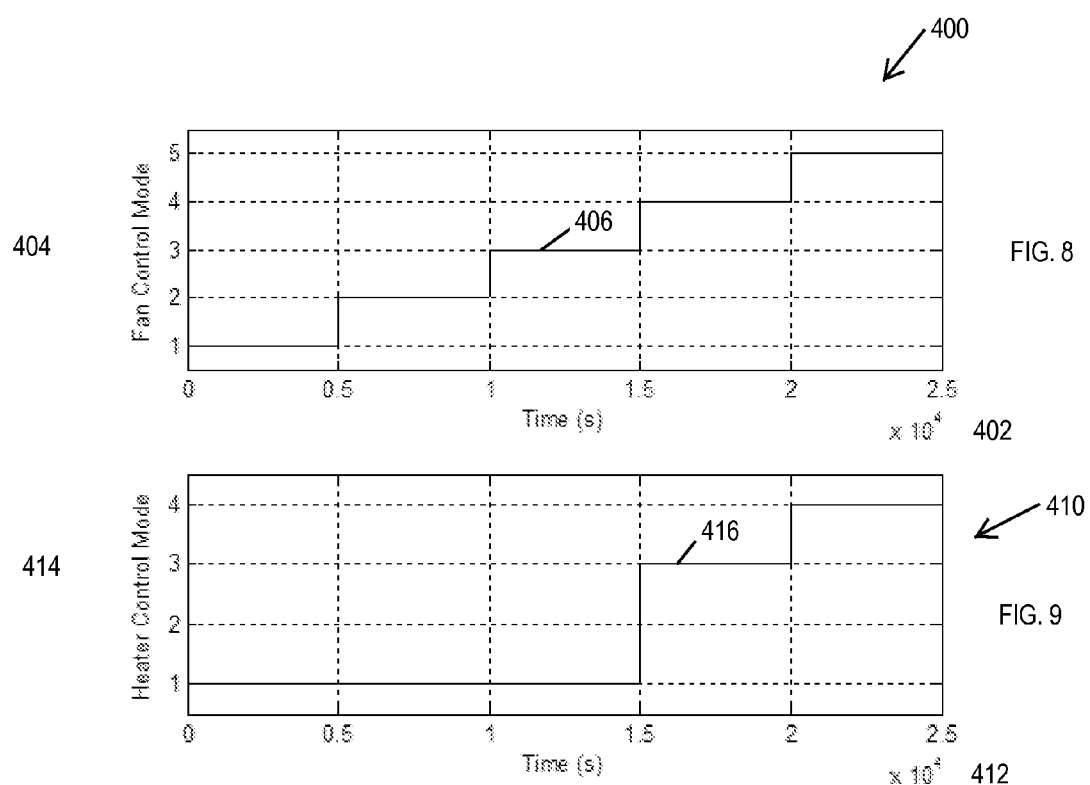

LIQUID COOLED THERMAL CONTROL SYSTEM FOR AN IMAGING DETECTOR

BACKGROUND OF THE INVENTION

The subject matter described herein relates generally to imaging detectors, such as computed tomography (CT) detectors, and more particularly, to a fault tolerant cooling system for CT detectors.

CT detectors may include a detector rail having a plurality of detector components positioned thereon. The detector components also may include a collimator having openings formed therein to direct x-rays emitted from a subject to a scintillator. The collimator separates the x-rays along the scintillator. The x-rays are then converted to light waves with a plurality of photodiodes positioned behind the scintillator. An analog-to-digital convertor converts the analog light waves to digital signals that are then used to generate an image of the subject.

In operation, the detector components may generate a considerable amount of heat which may affect the operation of the CT detector. For example, the heat may cause the detector components to shift on the detector rail. As such, the openings of the collimator may become misaligned with openings in the scintillator, leading to scatter or noise in the image generated by the CT imaging system. Additionally, some detector components are sensitive to changes in temperature. For example, the photodiodes may overheat or become damaged if exposed to large changes in temperature or cause image artifact due to increased electronic noise due to leakage current from photodiode and/or A/D device. This may be particularly problematic given that large amounts of heat may be generated by the analog-to-digital converter which is positioned adjacent to the photodiodes.

Accordingly, at least some known imaging systems include a cooling system to cool the CT detector. The cooling system may include, for example, fans, heat sinks, temperature sensors, or the like. In operation, the temperature sensors provide an indication of the various operational temperatures at certain points within the cooling system. However, when a single temperature sensor fails, at least one known imaging system is shut down. A technician may then be contacted to repair the failed temperature sensor. As a result, a single failed temperature sensor may cause the imaging system to be taken out of operation for an extended period of time until the technician can repair and/or replace the failed temperature sensor.

SUMMARY OF THE INVENTION

In one embodiment, a liquid cooled thermal control system for a computed tomography (CT) detector is provided. The control system includes a plurality of temperature sensors and a control mode selector module coupled to the plurality of temperature sensors. The control mode selector module is programmed to receive an input from the plurality of temperature sensors, identify the inputs as either valid inputs or invalid inputs, and determine an operational mode of the liquid cooled thermal control system based on the identified inputs.

In another embodiment, a computed tomography (CT) imaging system is provided. The CT imaging system includes a detector rail, an x-ray detector positioned on the detector rail, the x-ray detector including a plurality of detector components, at least some of the detector components configured to detect x-rays, and a cooling system providing cooling fluid to at least one of the x-ray detector or the detector rail. The cooling system includes a plurality of temperature sensors and a control mode selector module coupled to the plurality of temperature sensors. The control mode selector module is programmed to receive an input from the plurality of temperature sensors, identify the inputs as either valid inputs or invalid inputs, and determine an operational mode of the cooling system on the identified inputs.

In a further embodiment, a method of controlling an operation of a computed tomography (CT) detector cooling system is provided. The method includes receiving a plurality of temperature sensor inputs from a plurality of temperature sensors at a control mode selector module, identifying the inputs as either valid inputs or invalid inputs, and determining an operational mode of the cooling system based on the identified inputs.

BRIEF DESCRIPTION OF THE DRAWINGS

FIG. 8 is a graph of an operation of a control mode selector module in accordance with various embodiments.

FIG. 9 is another graph of the operation of the control mode selector module in accordance with various embodiments.

DETAILED DESCRIPTION OF THE INVENTION

Figure 1:
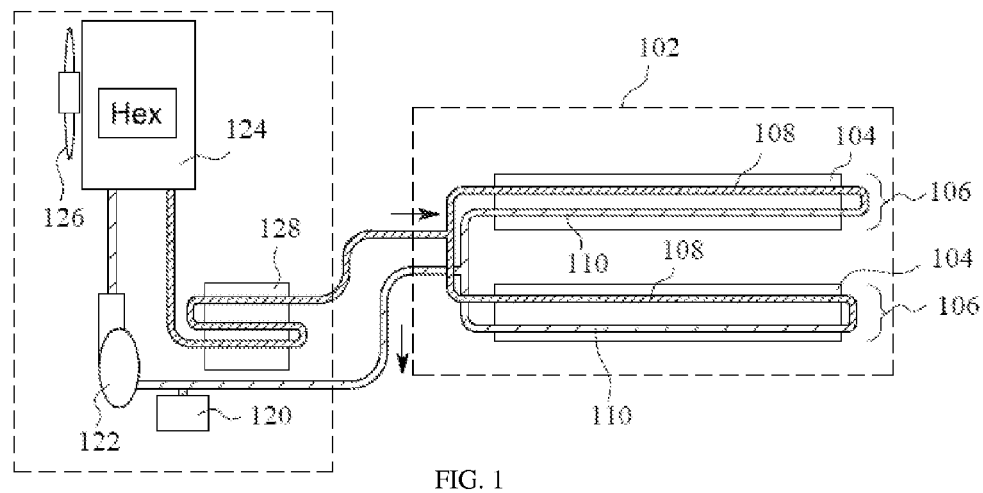
FIG. 1 is a schematic diagram of an exemplary cooling system that may be utilized to provide cooling for a detector in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Although various embodiments are described with respect to a computed tomography (CT) detector, it should be noted that the detector control system described herein may be modified for use with other detectors or systems. For example, a fault-tolerant detector control system may be utilized with a Positron Emission Tomography (PET) system, a Single Photon Emission Computed Tomography (SPECT) system, a Magnetic Resonance Imaging (MRI) system, and/or an X-ray system, among others.

FIG. 1 is a schematic diagram of an exemplary cooling system 100 that may be utilized to provide cooling for a detector illustrated as a CT detector 102. The cooling system 100 is in thermal communication with a plurality of detector rails 104 of the CT detector 102. In particular, cooling channels 106 of the cooling system 100 are in thermal communication with the detector rails 104. In various embodiments, the cooling channels 106 include a cool channel 108 and a hot channel 110. In one embodiment, the cooling channels 106 may extend through the detector rails 104. Optionally, a cold plate (not shown) may be coupled to the detector rails 104 and the cooling channels 106 may extend through the cold plate. In another embodiment, the cooling channels 106 may be configured to extend both through the detector rails 104 and the cold plate. The cooling channels 106 have cooling fluid flowing therethrough, which may be any suitable cooling fluid (e.g. liquid or gas).

In various embodiments, the cooling system 100 includes an accumulator 120 and a pump 122 that are positioned downstream from the cooling channels 106. In operation, the accumulator 120 receives cooling fluid from the cooling channels 106. The amount of cooling fluid received in the accumulator 120 may depend on a pressure of the cooling fluid within the cooling system 100, as described below. The pump 122 is positioned downstream of the accumulator 120 to control a flow of the cooling fluid thorough the cooling system 100. The pump 122 may be a single speed pump or a variable speed pump.

In operation, the pump 122 discharges the cooling fluid downstream to a heat exchanger 124. The heat exchanger 124 may be any suitable heat exchanger, for example, an air-to-liquid heat exchanger or a liquid-to-liquid heat exchanger. In the illustrated embodiment, the heat exchanger 124 is an air-to-liquid heat exchanger having a fan 126. The cooling fluid flows from the heat exchanger 124 downstream to an inline heater 128. The inline heater 128 may be an electric heater, a gas heater, or any other suitable heater. The inline heater 128 discharges the cooling fluid downstream to the cooling channels 106.

During operation, the cooling channels 106 receive the cooling fluid from the inline heater 128. The cooling fluid is provided at a predetermined temperature that is configured to maintain a temperature of the detector rails 104. More specifically, the cooling fluid in the cool channels 108 cools the detector rails 104 by receiving heat from the detector rails 104 through at least one of thermal conduction or convection. The heated cooling fluid then flows through the hot channels 110 downstream to the accumulator 120. The accumulator 120 stores a portion of the cooling fluid based on a pressure within the cooling system 100. For example, when the cooling system 100 is operating at a higher pressure, the accumulator 120 may store more cooling fluid than when the cooling system 100 is operating at a lower pressure. The accumulator 120 stores the cooling fluid to maintain a substantially constant operating pressure of the cooling system 100. The accumulator 120 accounts for expansion of the cooling fluid at high pressures and may be utilized to pressurize the pump 122, thereby, preventing cavitation within the pump 122.

The pump 122 receives cooling fluid from the accumulator 120. The pump 122 may be a variable speed pump that is controlled to adjust an amount of cooling fluid discharged to the heat exchanger 124. By controlling a speed of the pump 122, a temperature of the cooling fluid may be controlled. For example, increasing a speed of the pump 122 increases the liquid flow rate as the cooling fluid travels through the heat exchanger 124, which increases the cooling rate. Conversely, decreasing a speed of the pump 122 decreases the liquid flow rate as the cooling fluid flows through the heat exchanger 124, which decreases the cooling rate. In one embodiment, the pump 122 discharges the cooling fluid to the heat exchanger 124 at a flowrate that is configured to achieve the predetermined temperature of the cooling fluid.

In the illustrated embodiment, the heat exchanger 124 receives the cooling fluid from the pump 122. The heat exchanger 124 reduces the temperature of the cooling fluid to a temperature that is below the predetermined temperature. The fan 126 of the heat exchanger 124 may be controlled to adjust the temperature of the cooling fluid. For example, the fan 126 may be operated at a higher speed to reduce the temperature of the cooling fluid. Conversely, the fan 126 may be operated at a lower speed to increase the temperature of the cooling fluid. The speed of the fan 126 is controlled to achieve cooling of the cooling fluid to below the predetermined temperature.

The cooling fluid is discharged from the heat exchanger 124 downstream to the inline heater 128. The inline heater 128 increases the temperature of the cooling fluid from below the predetermined temperature to the predetermined temperature. In operation, the inline heater 128 is capable of fine tuning the temperature of the cooling fluid, whereas, the heat exchanger 124 may not be capable of providing regulation and control of temperatures. Accordingly, the heat exchanger 124 is utilized to reduce the temperature of the cooling fluid to below the predetermined temperature. The inline heater 128 then fine tunes the temperature of the cooling fluid to achieve the predetermined temperature. The power supplied to the inline heater 128 may be controlled to adjust the temperature of the cooling fluid. By adjusting the power supplied to the inline heater 128, the heat produced by the inline heater 128 is adjusted. For example, the inline heater 128 may be operated at a higher power to increase the temperature of the cooling fluid. Conversely, the inline heater 128 may be operated at a lower power to reduce the temperature of the cooling fluid. The inline heater 128 discharges the cooling fluid into the cool channels 106 at the predetermined temperature to maintain a temperature of the detector rails 104.

Accordingly, in various embodiments, the cooling system 100 is utilized to maintain a temperature of the detector rails 104 at a steady-state temperature. Moreover, the cooling system 100 facilitates reducing or preventing changes in the temperature of the detector rails 104. The cooling system 100 may adjust several parameters to control the temperature of the cooling fluid. For example, any one of a speed of the pump 122, a speed of the fan 126, or a power of the inline heater 128 may be adjusted to achieve the predetermined temperature of the cooling fluid.

Figure 2:
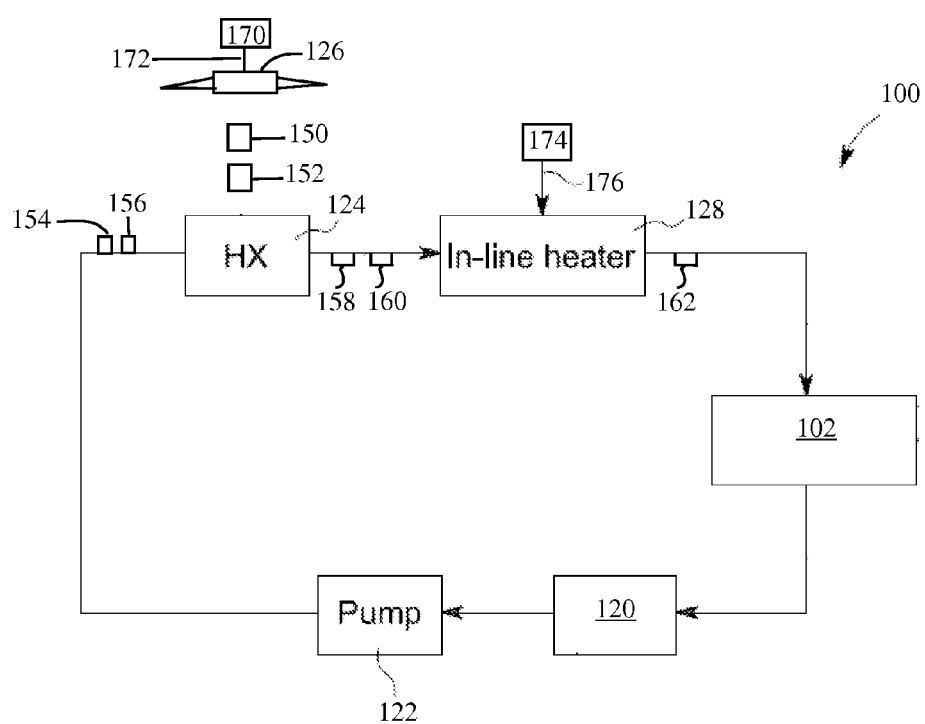
FIG. 2 illustrates a detailed block diagram of the cooling system shown in FIG. 1.

FIG. 2 illustrates a detailed block diagram of the cooling system 100 shown in FIG. 1. As described above, the cooling system 100 includes the accumulator 120, the pump 122, the heat exchanger 124, the fan 126, and the inline heater 128. The cooling system 100 also includes a plurality of temperature sensors that are disposed at various positions in the cooling system 100. In various embodiments, the cooling system includes a first air temperature sensor 150 and a second air temperature sensor 152. In the exemplary embodiment, the first and second air temperature sensors 150 and 152 are disposed proximate to the fan 126 and are configured to output an electrical signal that indicates a temperature of the air entering the heat exchanger 124, i.e. the ambient air temperature. In various embodiments, the temperature sensors 150 and 152 therefore are redundant temperature sensors which each indicate the ambient air temperature.

The cooling system 100 also includes a third temperature sensor 154 and a fourth temperature sensor 156. In the exemplary embodiment, the third and fourth temperature sensors 154 and 156 are disposed proximate to an inlet of the heat exchanger 124 and are configured to output an electrical signal that indicates a temperature of the cooling fluid entering the heat exchanger 124. In various embodiments, the temperature sensors 154 and 156 therefore are redundant temperature sensors which each indicate the temperature of the cooling fluid entering the heat exchanger 124.

The cooling system 100 also includes a fifth temperature sensor 158 and a sixth temperature sensor 160. In the exemplary embodiment, the fifth and sixth temperature sensors 158 and 160 are disposed proximate to an outlet of the heat exchanger 124 and are configured to output an electrical signal that indicates a temperature of the cooling fluid being discharged from the heat exchanger 124 and thus the temperature of the cooling fluid entering the inline heater 128. In various embodiments, the temperature sensors 158 and 160 therefore are redundant temperature sensors which each indicate the temperature of the cooling fluid being discharged from the heat exchanger 124.

The cooling system 100 also includes a seventh temperature sensor 162. In the exemplary embodiment, the seventh temperature sensor 162 is disposed proximate to an outlet of the inline heater 128 and is configured to output an electrical signal that indicates a temperature of the cooling fluid being discharged from the inline heater 128. In various embodiments, the cooling system 100 may also include an eighth temperature sensor (not shown) that also indicates a temperature of the cooling fluid being discharged from the inline heater 128. It should be realized that the temperature sensors shown in FIG. 2 are exemplary, and that the cooling system 100 may include additional temperature sensors not shown in FIG. 2. For example, the cooling system 100 may include additional temperature sensors that are installed in other positions on the cooling system 100.

The cooling system 100 includes a fan speed controller 170. In operation, the fan speed controller 170 is configured to control the operation of the fan 126. More specifically, the fan speed controller 170 is configured to transmit a signal 172 to the fan 126 that either increases, decreases, or maintains the operational speed of the fan 126. The cooling system 100 also includes a heater controller 174. In operation, the heater controller 174 is configured to control the operation of the inline heater 128. More specifically, the heater controller 174 is configured to transmit a signal 176 to the inline heater 128 that either increases, decreases, or maintains the operational temperature of the fluid being discharged from the inline heater 128.

Figure 3:
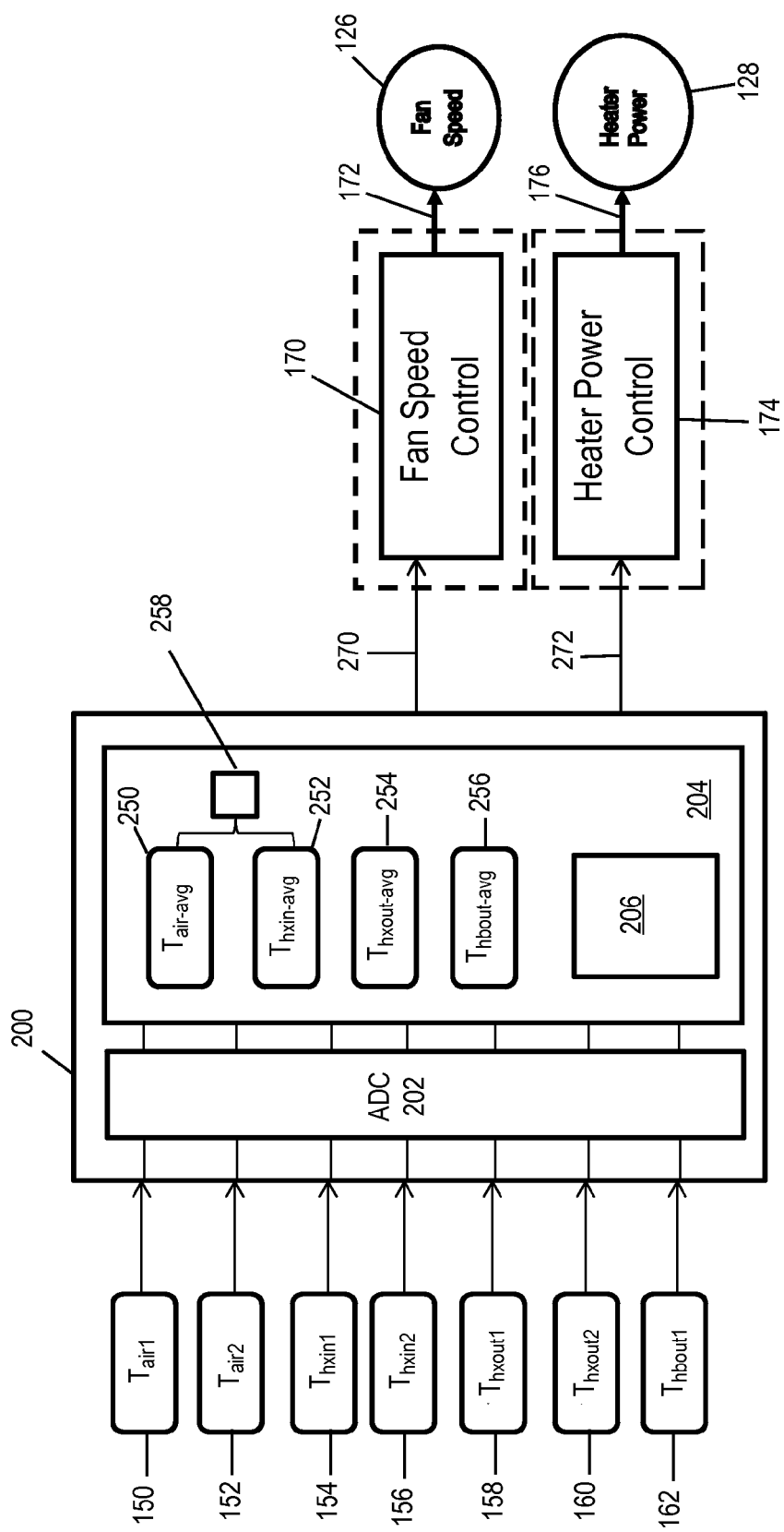
FIG. 3 is a block diagram of an exemplary fault-tolerant control system that may be formed in accordance with various embodiments.

FIG. 3 is a block diagram of an exemplary fault-tolerant control system 200 that may be utilized to control the operation of a cooling system, such as for example, the cooling system 100 shown in FIGS. 1 and 2. In various embodiments, the control system 200 includes an analog-to-digital (A/D) converter 202. In operation, the A/D converter 202 receives analog data from the sensors detectors 150-162 and converts the analog signals to digital signals for subsequent processing. In various embodiments, the digital signals output from the A/D converter 202 are input to a control mode selector module 204. In operation, the control mode selector module 204 is configured to receive digital inputs from the A/D converter 202 and then select and implement a control mode based on the received digital signals. The control mode selector module 202 may be implemented as a piece of hardware, such as a processor 206. Optionally, the control mode selector module 204 may be implemented as a set of instructions that are installed on the processor 206. The set of instructions may be stand alone programs, may be incorporated as subroutines in an operating system installed on the processor 206, may be functions that are installed in a software package on the processor 206, or may be a combination of software and hardware. It should be understood that the various embodiments are not limited to the arrangements and instrumentality shown in the drawings.

In operation, the control mode selector module 204 is configured to perform various methods described herein. Accordingly, the control mode selector module 204 may operate the cooling system in various operational modes or configurations based on the inputs received from the sensors 150-162. For example, in various embodiments, the control mode selector module 204 is configured to control a temperature of the cooling fluid entering the detector 102 using all of the sensors 150-162, a portion of the sensors 150-162, or only one of the sensors 150-162. Accordingly, the control mode selector module 204 enables the cooling system to remain operational when a single sensor has failed or multiple sensors have failed. In various embodiments, the control mode selector module 204 is configured to maintain the operational availability of the cooling system 100 using a plurality of valid sensors or only a single valid temperature sensor by changing the control scheme of the cooling system 100 while maintaining the temperature control for the detector 102.

For example, in various embodiments, the control mode selector module 204 is configured to detect sensor failures. More specifically, the control mode selector module 204 is configured to identify whether the sensors 150-162 are "valid" or "invalid". The term "invalid" as used herein refers to a sensor that is outputting a signal that is not representative of the actual temperature at the point where the sensor is located. In contrast, the term "valid" as used herein refers to a sensor that is outputting a signal that is representative of the actual temperature at the point where the sensor is located. For example, if the actual temperature of the air inlet to heat exchanger 124 is 80 degrees and the temperature sensor 150 is outputting a signal that indicates the air temperature is 30 degrees, the control mode selector module 204 is configured to identify the temperature sensor 150 as an "invalid" temperature sensor. In contrast, if the actual temperature of the air inlet to heat exchanger 124 is 80 degrees and the temperature sensor 150 is outputting a signal that indicates the air temperature is 78 degrees, the control mode selector module 204 is configured to identify the temperature sensor 150 as a "valid" temperature sensor. Thus a sensor may be considered valid when the output form the sensor falls within a predetermined range of values.

In various embodiments, the control mode selector module 204 may identify a sensor as "invalid" or "valid" based on comparing the output from the sensor to the outputs from other sensors and a priori information. For example, both temperature sensors 150 and 152 are used to provide a temperature of the air input to the heat exchanger 124. Accordingly, if the temperature sensor 150 is outputting 80 degrees and the temperature sensor 152 is outputting 20 degrees, the control mode selector module 204 may indicate that the temperature sensor 150 is "valid" and the temperature sensor 152 is "invalid". Moreover, to identify "invalid" and "valid" temperature sensors, the control mode selector module 204 may compare the outputs from other temperature sensors to each other or use a priori scales or tables of expected temperature values to identify "valid" and "invalid" temperature sensors.

In various embodiments, the control mode selector module 204 is also configured to average the temperature values output from various sensors together to generate an average temperature value at some locations. For example, as discussed above, the sensors 150 and 152 are each configured to output a signal that indicates the temperature of air entering the heat exchanger 124. Thus, the temperature sensor 152 is redundant to the temperature sensor 150. Accordingly, in the exemplary embodiment, the control mode selector module 204 is configured to initially identify whether the temperature sensors 150 and 152 are invalid or valid and then use this information to generate an average air temperature reading $T_{airavg}$ 250.

For example, assume that both temperature sensors 150 and 152 are determined to be "valid" temperature sensors. Moreover, assume that temperature sensor 150 is outputting a signal indicating a temperature of 78 degrees and the temperature sensor 152 is outputting a signal indicating a temperature of 82 degrees. In the exemplary embodiment, the control mode selector module 204 generates a $T_{airavg}$ 250 having a value of 80 degrees. In one embodiment, if the control mode selector module 204 determines that the temperature sensor 150 is invalid and the temperature sensor 152 is valid, the control mode selector module 204 is configured to set the $T_{airavg}$ 250 output equal to the temperature sensor 152 output, i.e. 82 degrees. In another embodiment, if the control mode selector module 204 determines that the temperature sensor 152 is invalid and the temperature sensor 150 is valid, the control mode selector module 204 is configured to set the $T_{airavg}$ 250 output equal to the temperature sensor 150 output, i.e. 78 degrees. In a further embodiment, if the control mode selector module 204 determines that the temperature sensors 150 and 152 are each invalid, the control mode selector module 204 is configured to identify $T_{airavg}$ 250 as invalid information. The use of the invalid information is described in more detail below.

The control mode selector module 204 is also configured to average the values output from the sensors 154 and 156. For example, as discussed above, the sensors 154 and 156 are each configured to output a signal that indicates the temperature of the cooling fluid entering the heat exchanger 124. Thus, the temperature sensor 154 is redundant to the temperature sensor 156. Accordingly, and as described above with respect to the temperature sensors 150 and 152, the control mode selector module 204 initially identifies whether the temperature sensors 154 and 156 are valid or invalid and then uses this information to generate an average air temperature reading $T_{hxin-avg}$ 252.

Accordingly, if the temperature sensors 154 and 156 are each valid, $T_{hxin-avg}$ 252 is an average value of the outputs from both temperatures sensors 154 and 156. If temperature sensor 154 is invalid, $T_{hxin-avg}$ 252 is set equal to temperature sensor 156. If temperature sensor 156 is invalid, $T_{hxin-avg}$ 252 is set equal to temperature sensor 154. Moreover, if both temperature sensors 154 and 156 are invalid, the control mode selector module 204 is configured to identify $T_{hxin-avg}$ 252 as invalid information.

The control mode selector module 204 is also configured to average the values output from the sensors 158 and 160. For example, as discussed above, the sensors 158 and 160 are each configured to output a signal that indicates the temperature of the cooling fluid being discharged from the heat exchanger 124. Thus, the temperature sensor 158 is redundant to the temperature sensor 160. Accordingly, and as described above with respect to temperature sensors 150 and 152, the control mode selector module 204 initially identifies whether the temperature sensors 158 and 160 are invalid or valid and then uses this information to generate an average temperature reading $T_{hxout-avg}$ 254.

Accordingly, if the temperature sensors 158 and 160 are each valid, $T_{hxout-avg}$ 254 is an average value of the outputs from both temperatures sensors 158 and 160. If temperature sensor 158 is invalid, $T_{hxout-avg}$ 254 is set equal to the temperature sensor 160. If temperature sensor 160 is invalid, $T_{hxout-avg}$ 254 is set equal to the temperature sensor 158. Moreover, if both temperature sensors 158 and 160 are invalid, the control mode selector module 204 is configured to identify $T_{hxout-avg}$ 254 as invalid information.

In the exemplary embodiment, the cooling system 100 includes only a single sensor, sensor 162 that indicates a temperature of the fluid being discharged from the inline heater 128. Accordingly, in the exemplary embodiment, the selector module 204 is also configured to generate a signal $T_{hbout-avg}$ 256 that is set equal to the output from temperature sensor 162 assuming that the temperature sensor 162 is determined to be valid. If the temperature sensor 162 is invalid, the control mode selector module 204 is configured to identify $T_{hbout-avg}$ 256 as invalid information.

In various embodiments, the control mode selector module 204 is also configured to generate an initial temperature difference (ITD) signal 258 that indicates a temperature difference between the average air temperature entering the heat exchanger 124 ($T_{air-avg}$ 250) and the temperature of the cooling fluid entering the heat exchanger 124 ($T_{hxin-avg}$ 252). In the exemplary embodiment, ITD 258=$T_{hxin-avg}$ 252−$T_{air-avg}$ 250. The control mode selector module 204 therefore generates various temperature values that are indicative of the temperature of the air and/or cooling fluid at various points in the cooling system 100. Although the exemplary embodiment, is described with respect to temperatures $T_{air-avg}$ 250, $T_{hxin-avg}$ 252, $T_{hxout-avg}$ 254, $T_{hbout-avg}$ 256, and ITD 258, it should be realized that other combinations or temperature sensors may be utilized and that the temperatures $T_{air-avg}$ 250, $T_{hxin-avg}$ 252, $T_{hxout-avg}$ 254, $T_{hbout-avg}$ 256, and ITD 258 are exemplary only. Accordingly, in the exemplary embodiment, the control mode selector module 204 is configured to identify each of the sensors 150-162 as either "valid" or "invalid" and generate the signals $T_{air-avg}$ 250, $T_{hxin-avg}$ 252, $T_{hxout-avg}$ 254, $T_{hbout-avg}$ 256, and ITD 258 as described above.

In various embodiments, at least a portion of the outputs from the sensors 150-162 are utilized by the fault-tolerant control system 200 to maintain the operational temperature of the cooling fluid and thus maintain a temperature of the detector rails 104 at the steady-state temperature. More specifically, the control mode selector module 204 is configured to utilize the sensor inputs 150-162, and the valid and invalid information derived for each of the sensor inputs 150-162 to select and implement an operational control mode based on the signals. In operation, the control mode selector module 204 is configured to generate a signal 270 to control the operation of the fan controller 170. The control mode selector module 204 is also configured to generate a signal 272 to control the operation of the heater controller 174.

Figure 4:
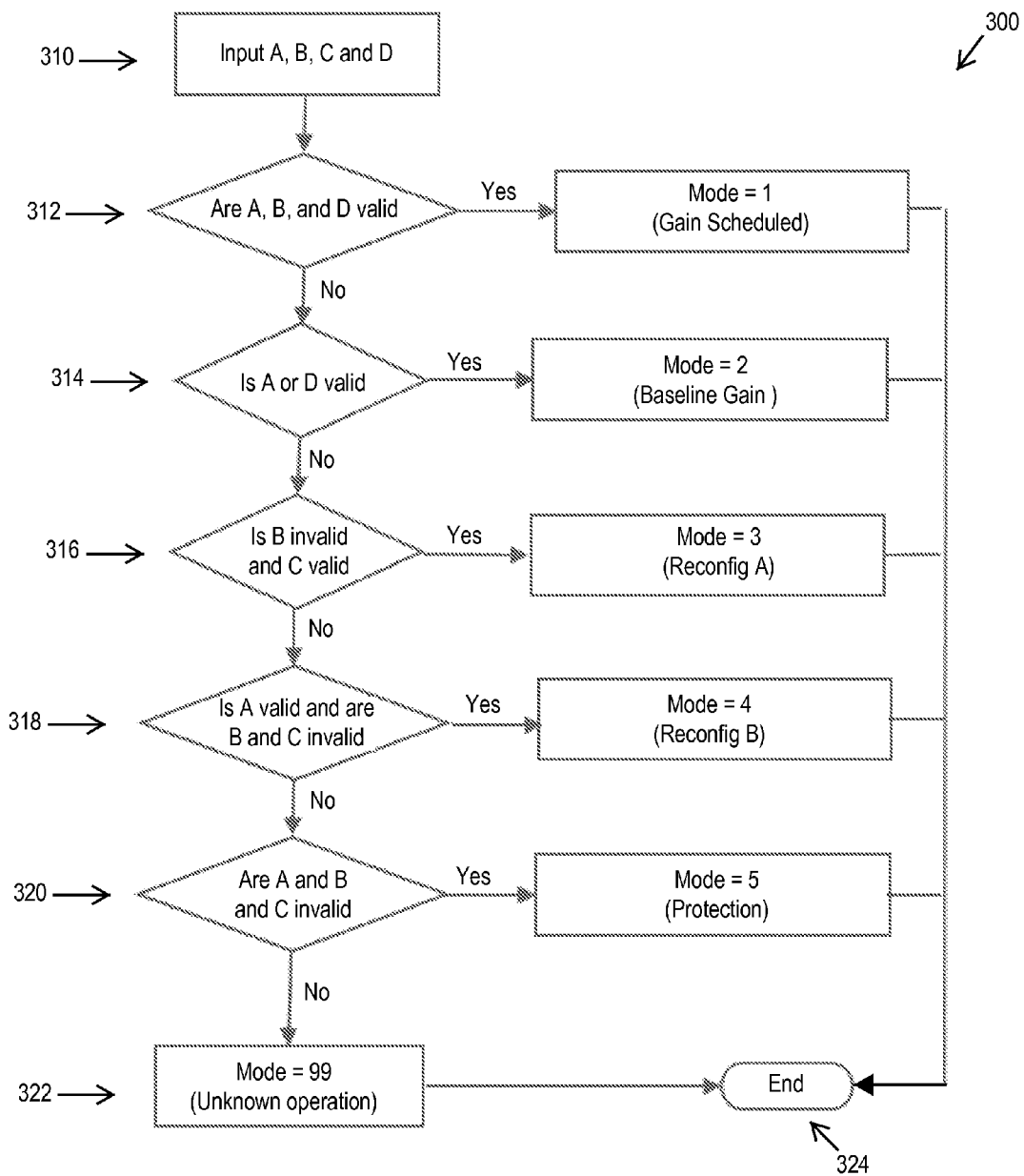
FIG. 4 is a logic flow chart of an exemplary method of controlling the operation of the cooling system shown in FIG. 1.
Figure 5:
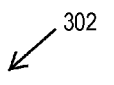
FIG. 5 is a table of the logic flow chart shown in FIG. 4.

FIG. 4 is a logic flowchart 300 illustrating an exemplary embodiment of a method to control the operation of the fan controller 170, and thus the operation of the fan 126. In various embodiments, the logic flowchart 300 may be implemented as a set of instructions that are installed on the control mode selector module 204. FIG. 5 is an exemplary table 302 illustrating the different operational modes that may be selected by the control mode selector module 204 based on the received inputs. In various embodiments, the control mode selector module 204 is configured to utilize a first subset of the sensors 150-162 to control the operation of the fan 126. In various embodiments, the first subset includes $T_{hxin-avg}$ 252, $T_{hxout-avg}$ 254, $T_{hbout-avg}$ 256, and $T_{air-avg}$ 250. As shown in FIGS. 4 and 5, the label A in the flow chart 300 is the $T_{hxin-avg}$ 252, the label B is the $T_{hxout-avg}$ 254, the label C is the $T_{hbout-avg}$ 256, and the label D is the $T_{air-avg}$ 250. Optionally, label A may also be the ITD 258. Moreover, in the table 302, the label 0 in the columns for the various sensors indicates that the sensor information is valid. For example, as shown in Table 302, the $T_{air-avg}$ 250 value of "0" indicates that at least one of the air sensors 150 or 152 is generating valid information, etc. Moreover, the label "1" indicates that neither of the air sensors 150 or 152 is generating valid information, thus the average air sensor output $T_{air-avg}$ 250 is invalid information.

In operation, at 310, the inputs A, B, C, and D are received. At 312, the control mode selector module 204 determines if either the inputs A, B, and D are valid. In one embodiment, if the inputs A, B, and D are valid inputs, the control mode selector module 204 is configured to operate the fan controller 170 in Mode 1. In Mode 1, the control mode selector module 204 is configured to generate a signal, such as the signal 270, shown in FIG. 3 that is used to control the cooling fluid temperature output from the heat exchanger 124. In various embodiments, and as shown in the table of FIG. 5, the signal 270 is a gain scheduled signal that is calculated based on a difference in the cooling fluid temperature and the air temperature at the heat exchanger 124. At 312, if control mode selector module 204 determines that any of the inputs A, B, and D are invalid, the method proceeds to 314.

At 314, the control mode selector module 204 is configured to determine if the input A or the input D are valid inputs. In one embodiment, if either the input A or the input D is a valid input, the control mode selector module 204 is configured to operate the fan controller 170 in Mode 2. In Mode 2, the control mode selector module 204 is configured to generate a signal, such as the signal 270, shown in FIG. 3 that is used to control the cooling fluid temperature output from the heat exchanger 124. In various embodiments, and as shown in the table of FIG. 5, the signal 272 is not a gain scheduled signal, but rather is a baseline signal that is generated based on the difference in the cooling fluid temperature and the air temperature at the heat exchanger 124. At 314, if the control mode selector module 204 determines that neither of the inputs A or D is valid, the method proceeds to 316.

At 316, the control mode selector module 204 is configured to determine if the input B is invalid and the input C is valid. In one embodiment, if the input B is invalid and the input C is valid, the control mode selector module 204 is configured to operate the fan controller 170 in Mode 3. In Mode 3, the control mode selector module 204 is configured to generate a signal, such as the signal 270, shown in FIG. 3 that is used to control the cooling fluid temperature output from the heat exchanger 124. In various embodiments, and as shown in the table of FIG. 5, the signal 270 is based on the heater outlet liquid temperature $T_{hbout-avg}$ 256. More specifically, the $T_{hbout-avg}$ 256 signal is used to regulate the operation of the fan controller 170 to maintain the temperature of the cooling fluid at the predetermined temperature. At 316, if control mode selector module 204 determines that neither of the B is valid or C is invalid, the method proceeds to 318.

At 318, the control mode selector module 204 is configured to determine if the input A is valid and the inputs B and C are invalid. In one embodiment, if the input A is valid and the inputs B and C are invalid, the control mode selector module 204 is configured to operate the fan controller 170 in Mode 4. In Mode 4, the control mode selector module 204 is configured to generate a signal, such as the signal 270, shown in FIG. 3 that is used to control the cooling fluid temperature output from the heat exchanger 124. In various embodiments, and as shown in the table of FIG. 5, the signal 270 is based on the heater inlet liquid temperature $T_{hxin-avg}$ 252 because the heat exchanger outlet temperature $T_{hxout-avg}$ 254 and the inline heater temperature $T_{hbout-avg}$ 256 are not available or are invalid. More specifically, the $T_{hxin-avg}$ 252 signal is used to regulate the operation of the fan controller 170 to maintain the temperature of the cooling fluid at the predetermined temperature. At 318, if control mode selector module 204 determines that the input A is invalid and the inputs B and C are valid, the method proceeds to 320.

At 320, the control mode selector module 204 is configured to determine if the inputs A, B, and C are invalid. In one embodiment, if the inputs A, B, and C are invalid, the control mode selector module 204 is configured to operate the fan controller 170 in Mode 5. In Mode 5, also referred to herein as the Equipment protection mode, the control mode selector module 204 is configured to generate a signal, such as the signal 270, shown in FIG. 3 that is used to control the cooling fluid temperature output from the heat exchanger 124. In various embodiments, and as shown in the table of FIG. 5, the signal 270 is configured to set the operational speed of the fan 126 to for example 75% of the rated fan speed or whatever is applicable to keep the acoustic noise acceptable for system. Moreover, the control mode selector module 204 is configured to send the signal 272 to the heater controller 174 to shut down the inline heater 128. Thus, when the temperatures cannot be determined for the heat exchanger inlet or outlet cooling fluid temperature and the inline heater outlet temperature are not available, the control mode selector module 204 operates the cooling system in the equipment protection mode as described above. At 320, if the control mode selector module 204 determines that any of the inputs A, B, or C are valid, the method proceeds to 322, wherein the operation of the cooling system 100 is maintained in its present mode of operation, and a technician is contacted to evaluate the operation of the cooling system 100. At 324, the program ends.

Figure 6:
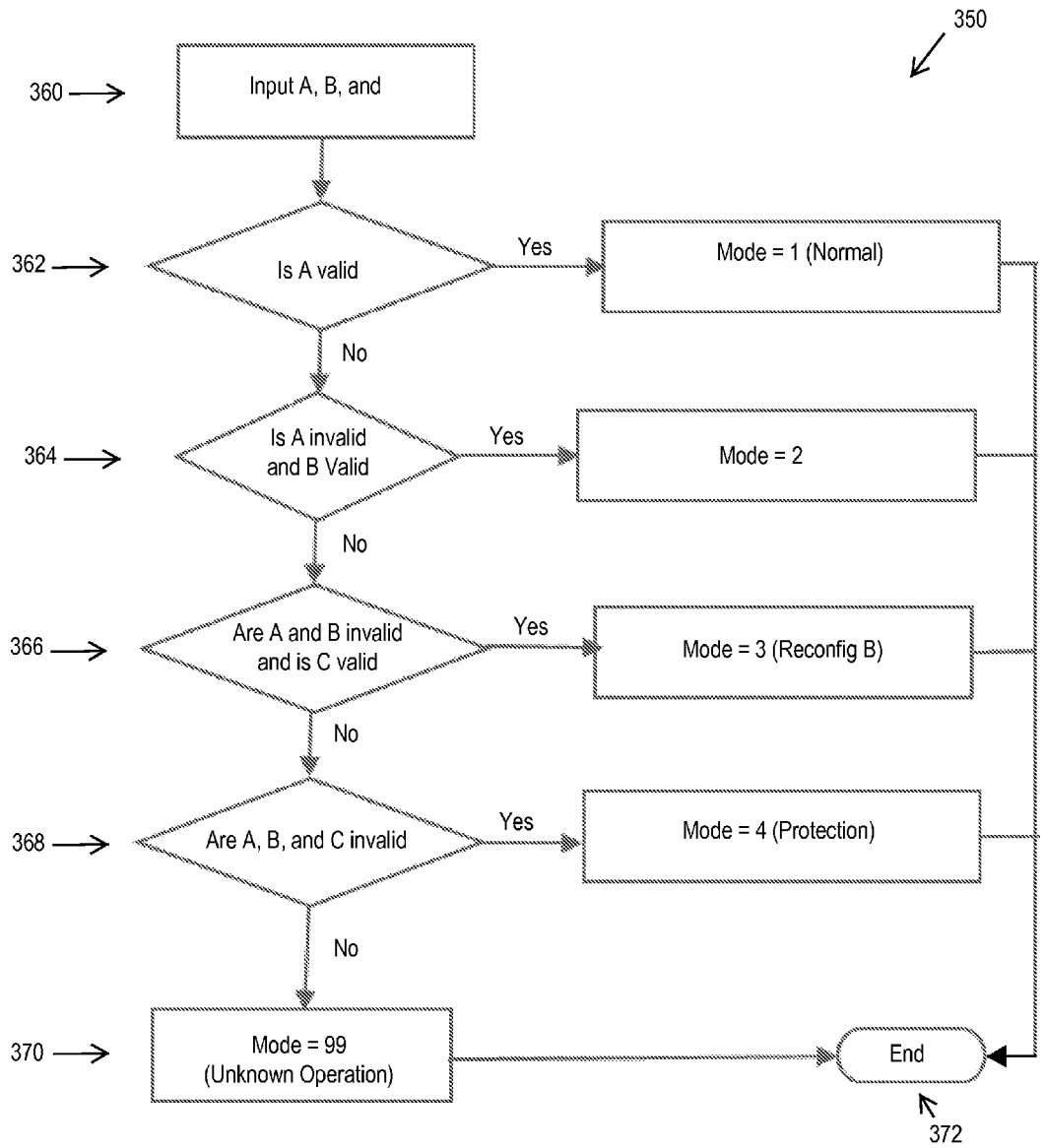
FIG. 6 is another logic flow chart of an exemplary method of controlling the operation of the cooling system shown in FIG. 1.
Figure 7:
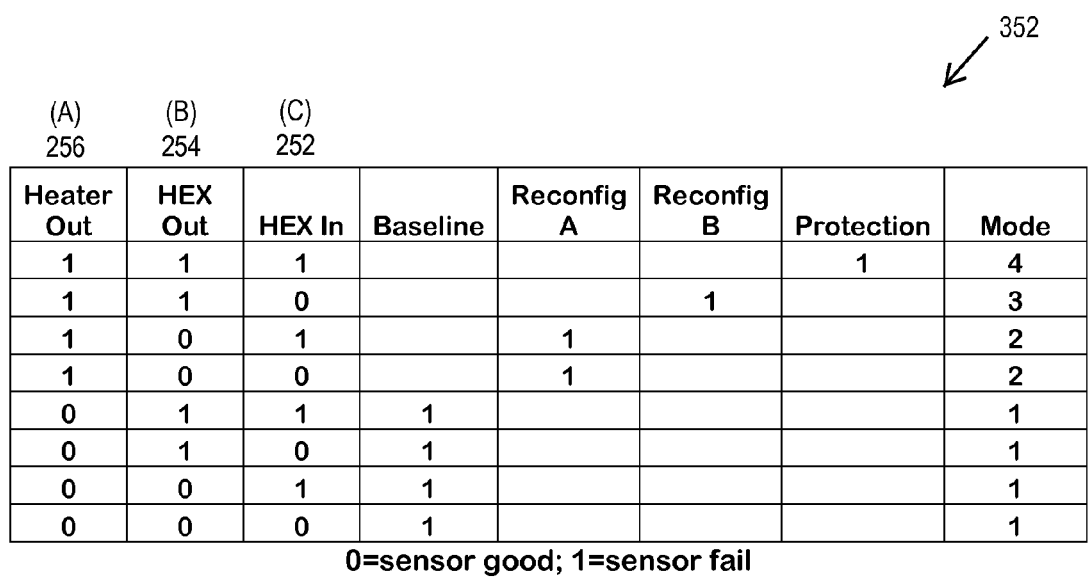
FIG. 7 is a table of the logic flow chart shown in FIG. 6.

FIG. 6 is a logic flowchart 350 illustrating an exemplary embodiment of a method to control the operation of the heater controller 174, and thus the operation of the inline heater 128. The logic flowchart 350 may be implemented as a set of instructions that are installed on the control mode selector module 204. FIG. 7 is an exemplary table 352 illustrating the different operational modes that may be selected by the control mode selector module 204 based on the received inputs. In various embodiments, the control mode selector module 204 is configured to utilize a second subset of the sensors 150-162 to control the operation of the inline heater 128. In various embodiments, the second subset includes $T_{hxin-avg}$ 252, $T_{hxout-avg}$ 254, and $T_{hbout-avg}$ 256. In the exemplary embodiment, and as shown in FIGS. 6 and 7, the label A in the flow chart 350 is the inline heater output temperature $T_{hbout-avg}$ 256, the label B is the heat exchanger output temperature $T_{hxout-avg}$ 254, and the label C is the heat exchanger input temperature $T_{hxin-avg}$ 252. Moreover, in the table 352, the label 0 in the columns for the various sensors indicates that the sensor information is valid. For example, as shown in Table 352, the $T_{hxin-avg}$ 252 value of "0" indicates that at least one of the temperature sensors 154 or 156 is generating valid information, etc. Moreover, the label "1" indicates that neither of the temperature sensors 154 or 156 is generating valid information, thus the average heat exchanger inlet temperature $T_{hxin-avg}$ 252 is invalid information.

Referring again to FIG. 6, at 360, the inputs A, B, and C are received. At 362, the control mode selector module 204 determines if the input A is valid. In one embodiment, if the input A is valid, the control mode selector module 204 is configured to operate the heater 174 in Mode 1. In Mode 1, also referred to herein as the baseline mode, the control mode selector module 204 is configured to generate a signal, such as the signal 272, shown in FIG. 3 that is used to control the operation of the inline heater 128 and thus control the temperature of the cooling fluid being discharged from the inline heater 128. In various embodiments, when the inline heater output temperature signal $T_{hbout-avg}$ 256 is valid, the inline heater 128 is adjusted based on the temperature of the cooling fluid output from the inline heater 128, i.e. the $T_{hbout-avg}$ 256 is used to adjust the inline heater 128. At 362, if the control mode selector module 204 determines that the input A is invalid, the method proceeds to 364.

At 364, the control mode selector module 204 is configured to determine if the input A is invalid and the input B is valid. In one embodiment, if the input A is invalid and the input B is valid, the control mode selector module 204 is configured to operate the heater 128 in Mode 2. In Mode 2, the control mode selector module 204 is configured to generate a signal, such as the signal 272, shown in FIG. 3 that is used to control the operation of the inline heater 128 and thus control the temperature of the cooling fluid being discharged from the inline heater 128. In various embodiments, when the inline heater output temperature signal $T_{hbout-avg}$ 256 is invalid and the heat exchanger outlet temperature $T_{hout-avg}$ 254 is available, the inline heater 128 is adjusted based on the temperature of the cooling fluid output from the heat exchanger 124, i.e. the $T_{hxout-avg}$ 254 signal is used to adjust the inline heater 128. At 364, if control mode selector module 204 determines that the input A is invalid and the input B is invalid, the method proceeds to 366.

At 366, the control mode selector module 204 is configured to determine if the inputs A and B are invalid and the input C is valid. In one embodiment, if the inputs A and B are invalid and the input C is valid, the control mode selector module 204 is configured to operate the heater 128 in Mode 3. In Mode 3, the control mode selector module 204 is configured to generate a signal, such as the signal 272, shown in FIG. 3 that is used to control the operation of the inline heater 128 and thus control the temperature of the cooling fluid being discharged from the inline heater 128. In various embodiments, when the inline heater output temperature signals $T_{hxout-avg}$ 254 and $T_{hbout-avg}$ 256 is invalid and the heat exchanger inlet temperature $T_{hxin-avg}$ 252 is available, the inline heater 128 is adjusted based on the temperature of the cooling fluid input to the heat exchanger 124, i.e. the $T_{hxin-avg}$ 252 signal is used to adjust the inline heater 128.

At 368, the control mode selector module 204 determines if the inputs A, B, and C are invalid. In one embodiment, if the inputs A, B, and C are invalid, the control mode selector module 204 is configured to operate the inline heater in Mode 4. In Mode 4, also referred to herein as the equipment protection mode, the control mode selector module 204 is configured to generate a signal, such as the signal 172, shown in FIG. 3 that is used to control the cooling fluid temperature output from the heat exchanger 124. In various embodiments, and as shown in the table of FIG. 5, the signal 172 is configured to set the operational speed of the fan 126 to 75% of the rated fan speed (or appropriate default speed to keep acoustic noise within requirements). Moreover, the control mode selector module 204 is also configured to send the signal 272 to the heater controller 174 to shut down the inline heater 128. Thus, when the temperatures can not be determined for the heat exchanger inlet, the heat exchanger outlet, or the inline heater outlet, the control mode selector module 204 operates the cooling system in the equipment protection mode as described above. At 370, if control mode selector module 204 determines that any of the inputs A, B, or C are indeterminate, the operation of the cooling system 100 is maintained in its present mode of operation, and a technician is contacted to evaluate the operation of the cooling system 100. At 364, the program ends.

FIG. 8 is a graph 400 representative of the performance of the control mode selector module 204. The x-axis 402 illustrates time in seconds and the y-axis 404 illustrates the various fan modes that may be selected by the control mode selector module 204. As shown in the graph 400, the line 406 illustrates the various modes of operation that be utilized to operate the fan 126 as shown in the flowchart of FIG. 4. In operation, the control mode selector module 204 substantially continuously monitors the operator of the sensors 150-162 to determine whether the sensors are valid or invalid. As shown in FIG. 8, the control mode selector module is able to shift the operational mode of the cooling system 100 in a short period of time after a sensor is identified as invalid.

FIG. 9 is another graph 410 representative of the operation of the inline heater 128. The x-axis 412 illustrates time in seconds and the y-axis 414 illustrates the various inline heater modes that may be selected by the control mode selector module 204. As shown in the graph 410, the line 416 illustrates the various modes of operation that be utilized to operate the inline heater 128 as shown in the flowchart of FIG. 6. As shown in FIG. 9, the control mode selector module is able to shift the operational mode of the cooling system 100 in a short period of time after a sensor is identified as invalid.

Figures 10, 11:
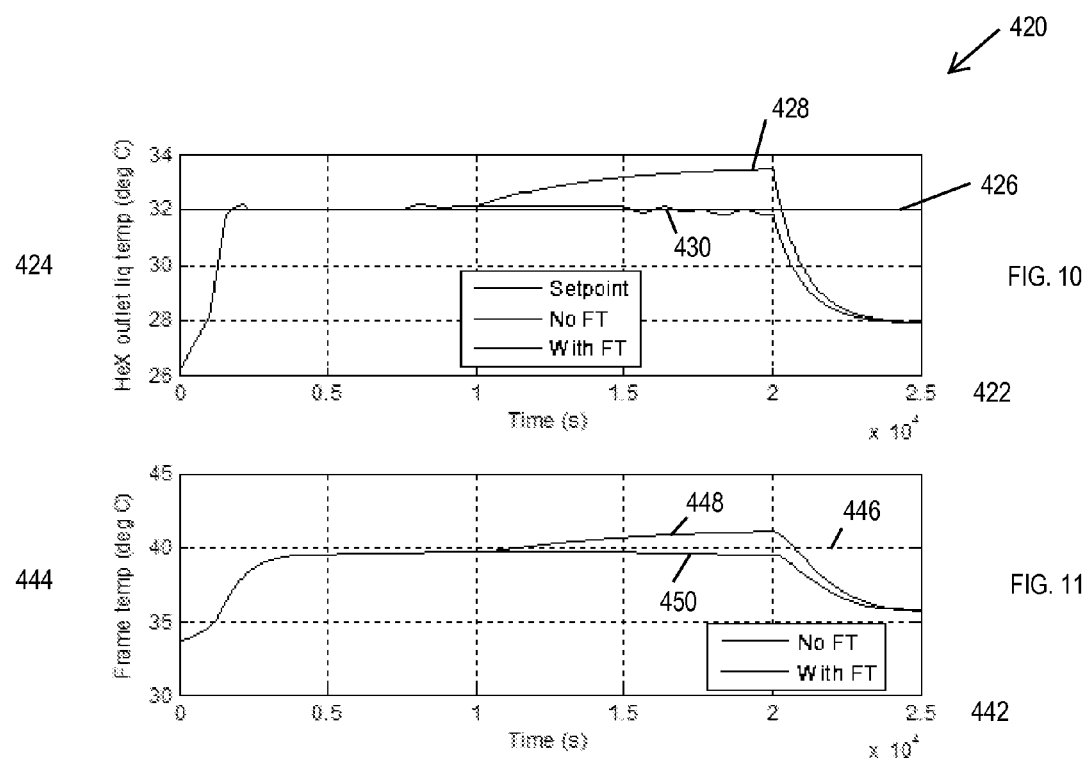
FIG. 10 is a graph illustrating a cooling performance of the control mode selector module in accordance with various embodiments.
FIG. 11 is another graph illustrating a cooling performance of the control mode selector module in accordance with various embodiments.

FIG. 10 is a graph 420 that illustrates the cooling performance of the control mode selector module 204 wherein an x-axis 422 is time and a y-axis is an outlet temperature of the cooling fluid being discharged from the heat exchanger 124 in degrees Celsius. Moreover, a value 426 represents a baseline temperature, or a predetermined temperature, at which the user desires to maintain the cooling fluid. A line 428 is a temperature at which the cooling fluid is maintained without the use of the control mode selector module 204 described above. A line 430 is an actual temperature at which the cooling fluid is maintained utilizing the control mode selector module 204 as described above. As shown in FIG. 10, the line 428 fluctuates from the baseline temperature 426 when the control mode selector module 204 is not utilized. However, when the control mode selector module 204 is utilized, the actual temperature, shown by the line 430, is maintained substantially equal to the desired temperature shown by the line 426.

FIG. 11 is a graph 440 that illustrates the cooling performance of the control mode selector module 204 wherein an x-axis 442 is time and a y-axis is a frame temperature of the detector shown in FIG. 1 in degrees Celsius. Moreover, a line 446 is a baseline temperature, or a predetermined temperature, at which the user desires to maintain the frame temperature. A line 448 is a temperature at which the cooling fluid is maintained without the use of the control mode selector module 204 described above. A line 450 is an actual temperature at which the cooling fluid is maintained utilizing the control mode selector module 204 described above. As shown in FIG. 11, the line 448 fluctuates from the baseline temperature 446 when the control mode selector module 204 is not utilized. However, when the control mode selector module 204 is utilized, the actual temperature, shown by the line 450 is maintained substantially equal to the desired temperature shown by the line 446.

Described herein is an exemplary control mode selector module that is configured to receive inputs from a plurality of temperature sensors monitoring a detector cooling system. The control mode selector module is programmed to automatically determine whether the temperature sensors are generating valid or invalid information. The control mode selector module is further programmed to automatically configure the cooling system in various operational modes based on the validity or invalidity of the information received from the temperature sensors.

A technical effect of various embodiments described herein is to provide a control scheme that provides fault tolerant control for any temperature sensor failure. The fault tolerant control is configured to maintain the cooling system availability using only a single operational temperature sensor. More specifically, the control scheme operates in various operational modes depending on the availability and location of the temperature sensors. As one or more temperature sensors fail, the control scheme enables the cooling system to remain operational until only a single operational temperature sensor is indicated to be a valid temperature sensor. The control scheme, in various embodiments, utilizes gain scheduling to vary the fan speed using a Proportional-Integral-Derivative (PID) control scheme when all the sensors are available. As the sensors fail the control mode is changed to achieve the required temperature control. Therefore, using multiple temperature sensors provide redundancy and enables the cooling system to be reconfigured to different operational modes based on the validity or invalidity of the various temperature sensors.

Figure 12:
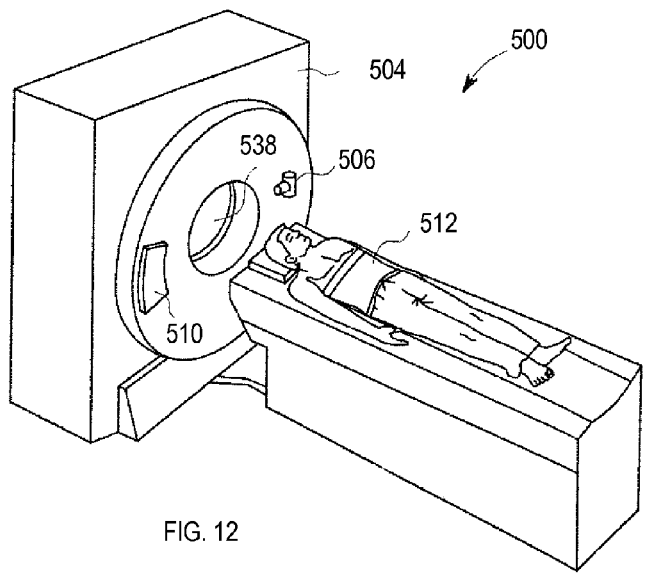
FIG. 12 is a pictorial drawing of a computed tomography (CT) imaging system constructed in accordance with various embodiments.
Figure 13:
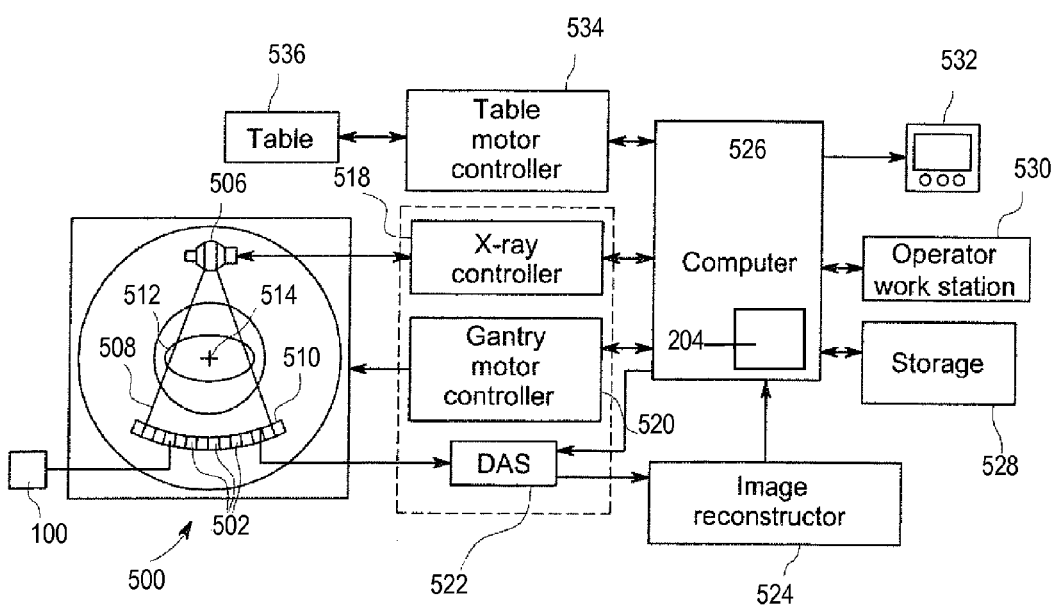
FIG. 13 is a schematic block diagram of the CT imaging system of FIG. 12.

The various methods and the control mode selector module may be implemented in an exemplary imaging system. For example, FIG. 12 is a pictorial view of a multi-modality imaging system that is formed in accordance with various embodiments. FIG. 13 is a block schematic diagram of a portion of the multi-modality imaging system shown in FIG. 12. Although various embodiments are described in the context of an exemplary dual modality imaging system that includes a CT imaging system and a positron emission tomography (PET) imaging system, it should be understood that other imaging systems capable of performing the functions described herein are contemplated as being used.

Referring to FIGS. 12 and 13, a multi-slice scanning imaging system, for example, a CT imaging system 500 is shown as including a plurality of the detectors 502 and in which the various embodiments may be implemented. The system 500 may be used with the liquid cooled thermal control systems described above. The CT imaging system 500 includes a gantry 504, which includes an x-ray source 506 (also referred to as an x-ray source 506 herein) that projects a beam of x-rays 508 toward a detector array 510 on the opposite side of the gantry 504. A cooling system, for example, the cooling system 100 described above, is in thermal contact with the detector array 510. The detector array 510 is formed by a plurality of detector rows (not shown) including a plurality of the detectors 502 that together sense the projected x-rays that pass through an object, such as a medical patient 512 between the array 510 and the source 506. Each detector 502 produces an electrical signal that represents the intensity of an impinging x-ray beam and hence can be used to estimate the attenuation of the beam as the beam passes through the patient 512. During a scan to acquire x-ray projection data, the gantry 504 and the components mounted therein rotate about a center of rotation 514. FIG. 13 shows only a single row of detectors 502 (i.e., a detector row). However, the multi-slice detector array 510 includes a plurality of parallel detector rows of detectors 502 such that projection data corresponding to a plurality of quasi-parallel or parallel slices can be acquired simultaneously during a scan.

Rotation of components on the gantry 504 and the operation of the x-ray source 506 are controlled by a control mechanism 516 of the CT imaging system 500. The control mechanism 516 includes an x-ray controller 518 that provides power and timing signals to the x-ray source 506 and a gantry motor controller 520 that controls the rotational speed and position of components on the gantry 504. A data acquisition system (DAS) 522 in the control mechanism 516 samples analog data from the detectors 502 and converts the data to digital signals for subsequent processing. An image reconstructor 524 receives sampled and digitized x-ray data from the DAS 522 and performs high-speed image reconstruction. The reconstructed image is applied as an input to a computer 526 that stores the image in a storage device 528. The image reconstructor 524 can be specialized hardware or computer programs executing on the computer 526. In various embodiments, the computer 526 may include the control mode selector module 204 described above.

The computer 526 also receives commands and scanning parameters from an operator via a console 530 that has a keyboard and/or other user input and/or marking devices, such as a mouse, trackball, or light pen. An associated display 532, examples of which include a cathode ray tube (CRT) display, liquid crystal display (LCD), or plasma display, allows the operator to observe the reconstructed image and other data from the computer 526. The display 532 may include a user pointing device, such as a pressure-sensitive input screen. The operator supplied commands and parameters are used by the computer 526 to provide control signals and information to the DAS 522, x-ray controller 518, and gantry motor controller 520. In addition, the computer 526 operates a table motor controller 534 that controls a motorized table 536 to position the patient 512 in the gantry 504. For example, the table 536 moves portions of the patient 512 through a gantry opening 538.

Various embodiments provide a thermal control system that may be mounted to and receive heat from detector rails and/or cold plates to receive heat from the detector components. The thermal control system has a controlled temperature (e.g. substantially constant temperatures) cooling fluid circulating therethrough to maintain the detector rails at a substantially constant predetermined temperature, for example, in response to one or more temperature sensor failures. The cooling fluid temperature is controlled in various embodiments using a heat exchanger, a fan directing air through the heat exchanger, an inline heater, and a pump that act as actuators for temperature control. A fan speed of the fan may be controlled using a control module based the cooling fluid temperature desired and actually measured. The inline heater power also may be modulated to control the cooling fluid temperature supplied to the detector rails. A pump speed also may be controlled to achieve a required cooling fluid flow rate through the thermal control system. At least one technical effect of some embodiments is maintaining a substantially constant detector electronics temperature.

Various embodiments described herein provide a tangible and non-transitory machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the described subject matter without departing from their scope. While the dimensions and types of materials described herein are intended to define the parameters of the various embodiments of the invention, the embodiments are by no means limiting and are exemplary embodiments. Many other embodiments will be apparent to one of ordinary skill in the art upon reviewing the above description. The scope of the various embodiments of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable one of ordinary skill in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A liquid cooled thermal control system, operating a fan and an in-line heater, to maintain a temperature of an imaging detector comprising:
    a plurality of temperature sensors positioned to sense a temperature of at least two from a group comprising of an air inlet of a heat exchanger, a liquid inlet of the heat exchanger, a liquid outlet of the heat exchanger, or a liquid outlet of the in-line heater; and
    a control mode selector module coupled to the plurality of temperature sensors, the control mode selector module being programmed to:
    receive an input from the plurality of temperature sensors;
    identify the inputs as either valid inputs or invalid inputs; and
    determine an operational mode of at least the fan or the in-line heater based on the identified inputs.

2. The liquid cooled thermal control system of claim 1, wherein the control mode selector module is further programmed to:
    select a first subset of the temperature sensors from the plurality of temperature sensors;
    identify the inputs from the first subset of temperature sensors as either valid inputs or invalid inputs; and
    determine an operational mode of the inline heater based on the identified subset of inputs.

3. The liquid cooled thermal control system of claim 2, wherein the control mode selector module is further programmed to:
    select a second different subset of temperature sensors from the plurality of temperature sensors;

identify the inputs from the second different subset of temperature sensors as either valid inputs or invalid inputs; and determine an operational mode of the fan based on the identified subset of inputs.

4. The liquid cooled thermal control system of claim 1, wherein the control mode selector module is further programmed to:

receive an input from a first temperature sensor;

automatically operate the liquid cooled thermal control system in a first operational mode when the input from the first temperature sensor is valid; and automatically operate the liquid cooled thermal control system in a second different operational mode when the input from the first temperature sensor is invalid.

5. The liquid cooled thermal control system of claim 1, wherein the control mode selector module is further programmed to:

automatically operate the liquid cooled thermal control system in a first operational mode based on a valid input received from a first temperature sensor;

automatically operate the liquid cooled thermal control system in a first operational mode based on an invalid input received from a first temperature sensor and a valid input received from a second temperature sensor.

6. The liquid cooled thermal control system of claim 1, said control mode selector module is further programmed to:

automatically control the operation of the fan using a first subset of the plurality of temperature sensors; and automatically control the operation of the inline heater using a different second subset of the plurality of temperature sensors.

7. The liquid cooled thermal control system of claim 1, wherein the mode selector module is further programmed to:

automatically control the operation of the fan using a heat exchanger inlet air temperature, a heat exchanger inlet cooling fluid temperature, a heat exchanger discharge cooling fluid temperature, and an inline heater discharge temperature; and automatically control the operation of the inline heater using the heat exchanger inlet cooling fluid temperature, the heat exchanger discharge cooling fluid temperature, and the inline heater discharge temperature.

8. The liquid cooled thermal control system of claim 1, wherein the mode selector module is further programmed to operate at least one of the fan or the inline heater in an equipment protection mode when each of the inputs are invalid inputs.

9. The liquid cooled thermal control system of claim 8, wherein to operate the fan or the inline heater in the equipment protection mode, the mode selector module is further programmed to:

de-energize the inline heater; and operate the fan at approximately seventy-five percent of the fan's rated operational speed.

10. The system of claim 1, wherein the control mode selector module is further programmed to determine an average temperature based on the valid inputs of at least two temperature sensors that are in the same position of the liquid cooled thermal control system.

11. The system of claim 1, wherein the control mode selector module further determines the operational mode of the fan or the in-line heater based on the combination of the position and validity of at least two temperature sensors;

such that the control mode selector module determines a first operational mode of the fan or in-line heater based on a first combination of the position and validity of the at least two temperature sensors;

such that the control mode selector module determines a second operational mode of the fan or in-line heater based on a second combination of the position and validity of the at least two temperature sensors; and such that the control mode selector module determines a third operational mode of the fan or in-line heater based on a third combination of the position and validity of the at least two temperature sensors.

12. The system of claim 11, wherein while the fan is in the first operational mode, the control mode selector module outputs a gain scheduled signal;

while the fan is in the second operational mode, the control mode selector module outputs a baseline gain signal; and while the fan is in the third operational mode, the control mode selector module outputs a reconfiguration signal.

13. The system of claim 12, wherein the gain scheduled signal is generated based on the difference of a heat exchanger liquid outlet temperature and a heat exchanger air inlet temperature;

wherein the baseline gain signal is generated based on the difference of the heat exchanger liquid outlet temperature and the heat exchanger air inlet temperature; and wherein the reconfiguration signal is generated based on an in-line heater output temperature or the heat exchanger liquid inlet temperature.

14. The system of claim 11, wherein while the in-line heater is in the first operational mode, the control mode selector module outputs a baseline gain signal;

while the in-line heater is in the second operational mode, the control mode selector module outputs a mode two signal; and while the in-line heater is in the third operational mode, the control mode selector module outputs a reconfiguration signal.

15. The system of claim 14, wherein the baseline gain signal is generated based on an in-line heater outlet temperature;

wherein the mode two signal is generated based on a heat exchanger liquid outlet temperature to control a heater controller; and wherein the reconfiguration signal that is generated is based on the heat exchanger liquid outlet temperature to control the heater controller.

16. A computed tomography (CT) imaging system comprising:

a detector rail;

an x-ray detector positioned on the detector rail, the x-ray detector including a plurality of detector components, at least some of the detector components configured to detect x-rays;

a cooling system providing cooling fluid to at least one of the x-ray detector or the detector rail, the cooling system comprising a plurality of temperature sensors positioned to sense a temperature of at least two from a group comprising of an air inlet of a heat exchanger, a liquid inlet of the heat exchanger, a liquid outlet of the heat exchanger, or a liquid outlet of an in-line heater; and a control mode selector module coupled to the plurality of temperature sensors, the control mode selector module being programmed to receive an input from the plurality of temperature sensors;

identify the inputs as either valid inputs or invalid inputs; and determine an operational mode of the cooling system based on the identified inputs.

17. The CT imaging system of claim 16, wherein the control mode selector module is further programmed to:
select a first subset of the temperature sensors from the plurality of temperature sensors;
identify the inputs from the first subset of temperature sensors as either valid inputs or invalid inputs; and
determine an operational mode of the in-line heater based on the identified subset of inputs.

18. The CT imaging system of claim 17, wherein the control mode selector module is further programmed to:
select a second different subset of temperature sensors from the plurality of temperature sensors;
identify the inputs from the second different subset of temperature sensors as either valid inputs or invalid inputs; and
determine an operational mode of a fan based on the identified subset of inputs.

19. The CT imaging system of claim 16, wherein the control mode selector module is further programmed to:
receive an input from a first temperature sensor;
automatically operate a liquid cooled thermal control system in a first operational mode when the input from the first temperature sensor is valid; and
automatically operate the liquid cooled thermal control system in a second different operational mode when the input from the first temperature sensor is invalid.

20. The CT imaging system of claim 16, wherein the control mode selector module is further programmed to:
automatically operate a liquid cooled thermal control system in a first operational mode based on a valid input received from a first temperature sensor;
automatically operate the liquid cooled thermal control system in a first operational mode based on an invalid input received from a first temperature sensor and a valid: input received from a second temperature sensor.

21. The CT imaging system of claim 16, wherein the control mode selector module is further programmed to:
automatically control the operation of a fan using a first subset of the plurality of temperature sensors; and
automatically control the operation of the inline heater using a different second subset of the plurality of temperature sensors.

22. The CT imaging system of claim 16, wherein the control mode selector module is further programmed to operate at least one of a fan or the inline heater in an equipment protection mode when each of the inputs are invalid inputs.

23. The CT imaging system of claim 22, wherein to operate the fan or the inline heater in the equipment protection mode, the mode selector module is further programmed to:
de-energize the inline heater; and
operate the fan at approximately seventy-five percent of the fan's rated operational speed or appropriately under acoustic noise level.

24. A method of controlling an operation of a fan and an in-line heater of a computed tomography (CT) detector cooling system to maintain the temperature of a CT detector comprising:
positioning a plurality of temperature sensors to sense a temperature of at least two from a group comprising an air inlet of a heat exchanger, a liquid inlet of the heat exchanger, a liquid outlet of the heat exchanger, or a liquid outlet of the in-line heater;
receiving a plurality of temperature sensor inputs from the plurality of temperature sensors at a control mode selector module;
identifying the inputs as either valid inputs or invalid inputs; and
determining an operational mode of at least the fan or the in-line heater based on the identified inputs.

25. The method of claim 24, further comprising:
selecting a first subset of temperature sensors from the plurality of temperature sensors;
identifying the inputs from the first subset of temperature sensors as either valid inputs or invalid inputs; and
determining an operational mode of the inline heater based on the identified subset of inputs.

26. The method of claim 25, further comprising:
selecting a second different subset of temperature sensors from the plurality of temperature sensors;
identifying the inputs from the second different subset of temperature sensors as either valid inputs or invalid inputs; and
determining an operational mode of the fan based on the identified subset of inputs.

* * * * *